United States Patent [19]
Lomholt

[11] Patent Number: 5,497,768
[45] Date of Patent: Mar. 12, 1996

[54] RESPIRATION CATHETER WITH SEALING CUFF AND GAS INFLATION CUT-OFF VALVE FOR CUFF

[76] Inventor: Vagn N. F. Lomholt, Lundevej 4, Allerød, Denmark, 3450

[21] Appl. No.: 234,720

[22] Filed: Apr. 28, 1994

Related U.S. Application Data

[63] Continuation of Ser. No. 890,591, Jul. 6, 1992, abandoned.

[30] Foreign Application Priority Data

Jan. 12, 1990 [DK] Denmark .................................. 0089/90

[51] Int. Cl.$^6$ ................... A61M 16/00; A61M 29/00; A62B 9/02; A62B 9/06
[52] U.S. Cl. .................. 128/207.16; 128/207.15; 128/911; 604/96; 604/99; 604/102
[58] Field of Search .................. 128/207.14–207.16, 128/911; 604/96–99, 102, 103

[56] References Cited

U.S. PATENT DOCUMENTS

| | | | |
|---|---|---|---|
| 3,709,227 | 1/1973 | Hayward | 128/207.15 |
| 3,769,983 | 11/1973 | Merav | 128/207.15 |
| 3,794,036 | 2/1974 | Carroll | 128/207.15 |
| 3,995,643 | 12/1976 | Merav | 128/207.15 |
| 4,119,101 | 10/1978 | Igich | 128/207.15 |
| 4,791,923 | 12/1988 | Shapiro | 128/207.15 |

FOREIGN PATENT DOCUMENTS

| | | | |
|---|---|---|---|
| 995542 | 8/1976 | Canada | 128/207.15 |
| 111149 | 6/1968 | Denmark . | |
| 9110464 | 7/1991 | WIPO | 128/207.16 |

*Primary Examiner*—Kimberly L. Asher
*Attorney, Agent, or Firm*—Merchant, Gould, Smith, Edell, Welter & Schmidt

[57] ABSTRACT

A respiration catheter has a sealing cuff (12) which encircles the catheter tube (10) and can be connected through a separate tube (13, 14) with a source of compressed air with a substantially constant pressure. This tube accommodates a cut-off valve (19, 20, 21) which is controlled by the pressure of the respiration air and is adapted to prevent air in the sealing cuff from escaping when this pressure exceeds the pressure in the source of compressed air. The position of this cut-off valve in the vicinity of the free end of the catheter tube obviates the disadvantageous effects of pressure drops in the catheter tube, which may occur when the valve is placed at the injection end of the catheter tube, as is the case in a known respiration catheter.

5 Claims, 2 Drawing Sheets

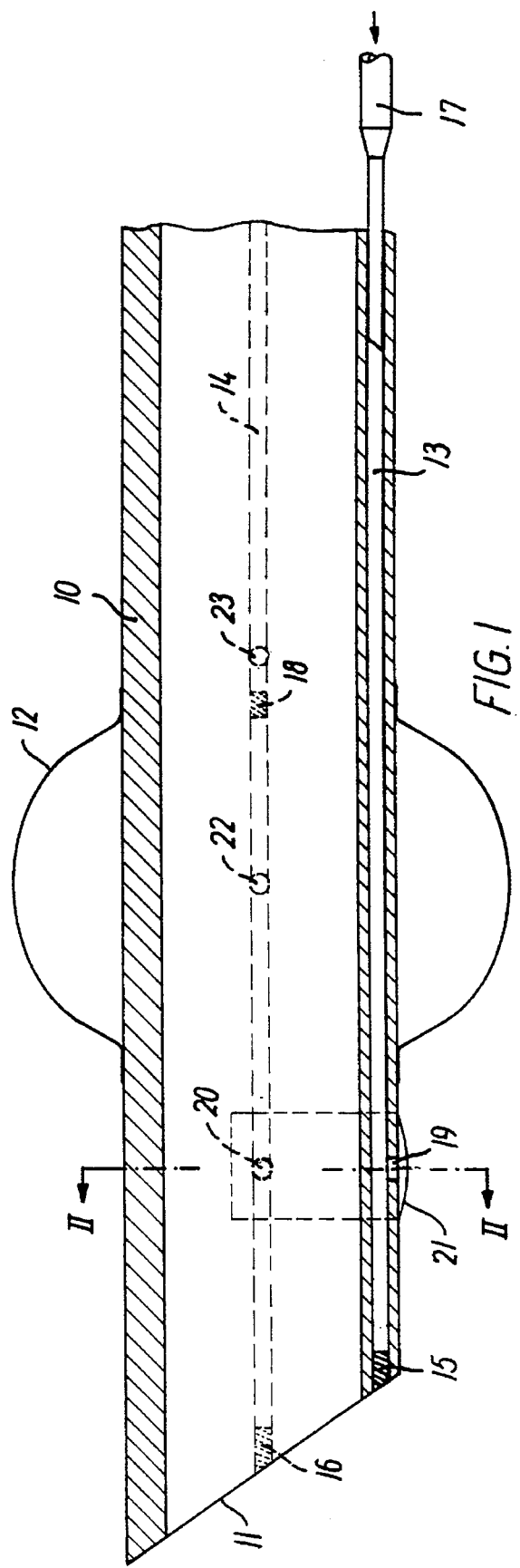
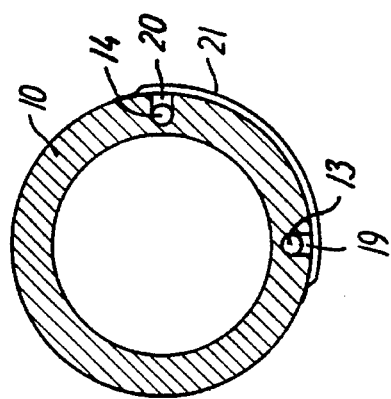
FIG.1
FIG.2

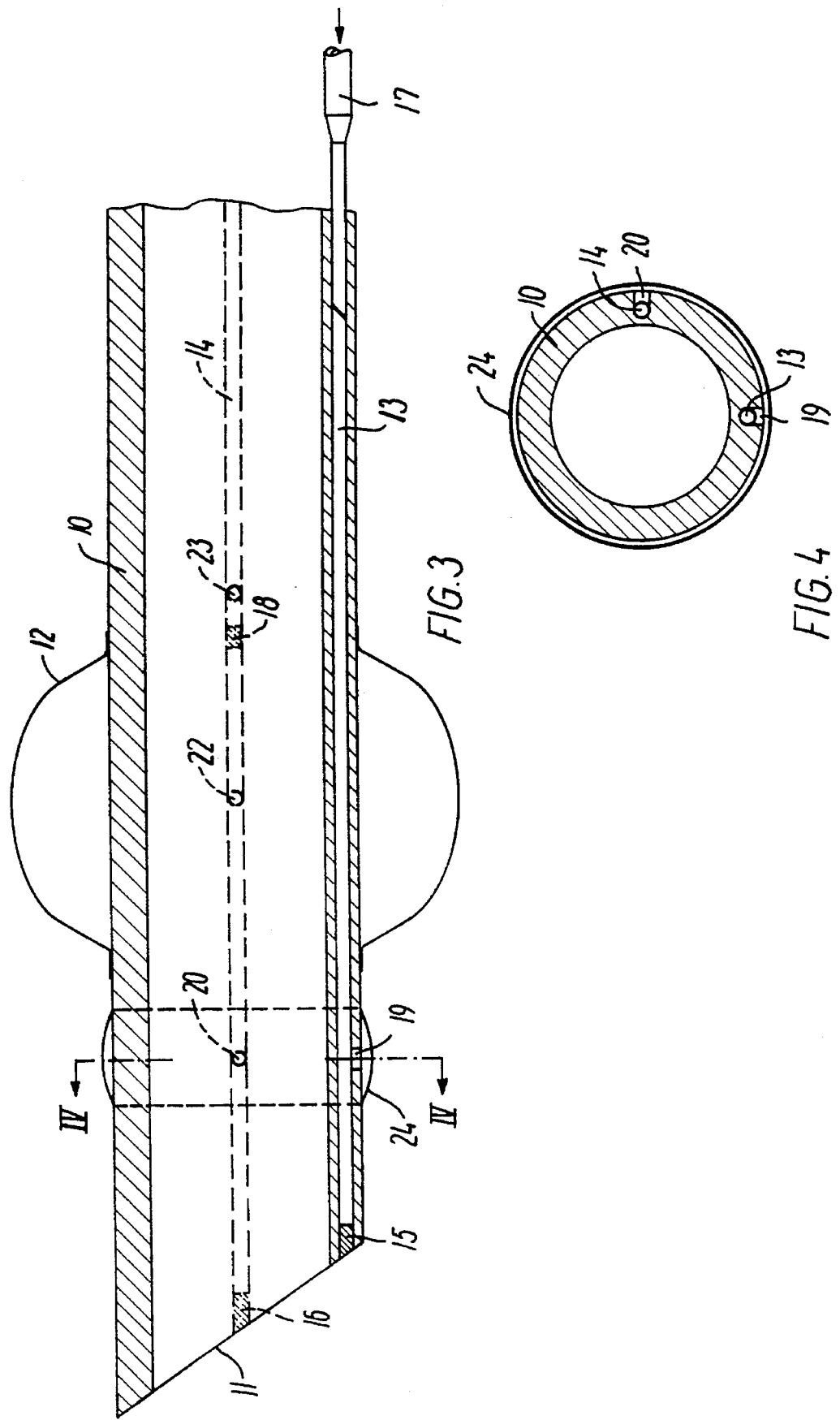

RESPIRATION CATHETER WITH SEALING CUFF AND GAS INFLATION CUT-OFF VALVE FOR CUFF

This is a continuation of application Ser. No. 07/890,591, filed Jul. 6, 1992, now abandoned.

FIELD OF THE INVENTION

The invention concerns a respiration catheter comprising a respiration tube for insertion into a patient's trachea. Such a respiration catheter is known from DK-C-111149.

BACKGROUND OF THE INVENTION

Endotracheal tubes intended for insertion through the mouth, nose or implanted in the neck (oro-naso and tracheostomy tubes) are usually provided with an inflatable cuff for sealing against the tracheal wall. The efficiency of the sealing is determined by the magnitude of the cuff pressure against the tracheal wall since the inflated cuff does not seal off pressures exceeding the pressure of the cuff against the wall. The air pressure in the cuff determines the pressure against the tracheal wall. The pressure of the cuff against the tracheal wall can be controlled and regulated only if the cuff has a sufficiently large diameter to make contact with the tracheal wall without any stretching of the sheet material of the cuff, i.e. the cuff must be lying folded on the tracheal wall. If this demand is met, the pressure in the cuff is identical with its pressure on the wall.

If the pressure of the cuff against the tracheal wall is considerably higher than 30 cm $H_2O$, the blood supply to the mucosa is occluded, and this causes damage in the form of superficial or deeper ulcerations after some time. This damage is prevented in that the sealing cuff, lying folded on the wall, is kept inflated from an outer pressure source with a constant, regulated pressure of 20 to 30 cm $H_2O$.

The sealing cuff has the additional function of preventing liquid (blood, saliva, vomit) from flowing past the cuff down into the lungs. It has been found that this function is accomplished when the pressure of the sealing cuff against the tracheal wall is at least 20 to 30 cm $H_2O$.

Spontaneous changes in the diameter of the trachea, changes in the catheter position and the diffusion of certain anaesthetic gases through the wall of the sealing cuff may cause considerable changes in the pressure in the sealing cuff if the inflation pressure is not controlled and regulated.

During artificial respiration the necessary pressure of the respiration air may often exceed 20 to 30 cm $H_2O$, and the pressure in the sealing cuff is then too low to seal off the pressure of the respiration air.

DESCRIPTION OF RELATED ART

In order for the sealing cuff to be able to seal off high inflation pressures during artificial respiration, the respiration catheter described in DK-C-111149 is equipped with a two-way cut-off valve mounted on the air supply tube for the sealing cuff. In this embodiment closing and opening of the valve are controlled by the pressure changes in the external opening of the catheter tube which are produced during artificial respiration. When the pressure in the catheter tube during inflation exceeds the constant, regulated pressure of 20 to 30 cm $H_2O$, the cut-off valve closes so that the air in the sealing cuff cannot escape through the air supply tube, and the pressure increase in the trachea is transferred to the sealing cuff, the air in the sealing cuff being compressed so that the sealing cuff can seal off the pressure prevailing in the trachea. When, during expiration, the pressure in the trachea decreases to 20 to 30 cm $H_2O$, the cut-off valve opens again, providing free connection between the source of compressed air and the sealing cuff, which then remains inflated by the constant, regulated pressure of 20 to 30 cm $H_2O$.

The respiration catheter according to DK-C-111149 has the closing valve arranged in a respiration air supply tube at the external opening of the catheter. Due to the flow resistance between the two ends of the catheter and the consequent difference in pressure, the valve closes prematurely during inflation and opens prematurely during expiration. This entails that part of the air in the sealing cuff escapes during the expiration phase so that, for a short moment, the cuff cannot provide an efficient sealing of the trachea.

SUMMARY OF THE INVENTION

The object of the invention is to provide an embodiment of a respiration catheter of the present type which prevents the said malfunction involving the risk of liquid flowing past the sealing cuff down into the lungs.

According to the present invention, a respiration catheter is provided comprising:

a respiration tube for insertion into a patient's trachea, the respiration tube having a distal end to face the patient's lungs when inserted in a patient's trachea, and a proximal end connected to a source of respiratory gas;

an inflatable sealing cuff encircling the respiration tube;

an inflation tube having a first end connected to the sealing cuff, and a second end connected to a source of compressed gas for inflating the sealing cuff; and a cut-off valve being accommodated in the inflation tube distally of the cuff, the cut-off valve having a first position and a second position, the first position being an open position, in which the sealing cuff communicates with the second end of the inflation tube, the second position being a closed position, in which the communication between the sealing cuff and the second end of the inflation tube is interrupted, the cut-off valve being in the second position in response to a pressure in the respiratory gas distally of the cuff exceeding gas pressure in the source of compressed gas.

In this structure, a pressure drop in the trachea cannot at any time cause premature opening of the closing valve and, consequently, neither undesirable escape of air from and thereby defective sealing capacity of the cuff.

BRIEF DESCRIPTION OF THE DRAWING

The invention will be described more fully below with reference to the drawings as follows:

FIG. 1 is a partly longitudinal cross-sectional view of a first embodiment of a respiration catheter in accordance with the present invention.

FIG. 2 is a cross-sectional view of the first embodiment of the respiration catheter along line II—II shown in FIG. 1.

FIG. 3 is a partly longitudinal cross-sectional view of a second embodiment of a respiration catheter in accordance with the present invention.

FIG. 4 is a cross-sectional view of the second embodiment of the respiration catheter along line IV—IV shown in FIG. 3.

DESCRIPTION OF THE PREFERRED EMBODIMENT

In the drawing, 10 is a catheter tube intended for introduction into a patient's trachea. Close to obliquely cut end 11 of the tube 10 is placed a sealing cuff 12, which is made of a thin, preferably inelastic sheet material and encircles the tube. Compressed air can be supplied to the cuff through a tubing system consisting of two channels 13 and 13, which are provided in the wall of the catheter tube 10, and which are closed by plugs 15 and 16, respectively, at the end of the tube 10. One channel 13 can be connected through a tube 17 to a source of compressed air (not shown) which delivers air with a substantially constant pressure, which may e.g. be of the order of 20 to 30 cm $H_2O$. Between the end 11 of the catheter tube 10 and the adjoining end of the cuff 12, each of the channels 13 and 14 is provided with holes 19 and 20, respectively, opening to the outside of the catheter tube, and these holes are covered by a rectangular piece 21 of sheet, which is welded along the edges to the catheter tube 10 and thus forms a valve which, controlled by the pressure conditions, can establish connection between the two holes 19 and 20 and interrupt this connection. The channel 14 communicates with the interior of the cuff 12 through another hole 22 positioned between the hole 20 and a plug 18. This channel additionally has a third hole 23 which is positioned immediately beyond the end of the cuff 12 facing away from tube end 11 and such that the plug 18 will be situated between the holes 22 and 23. This hole 23 opens to the outer side of the catheter tube 10.

When the shown catheter is introduced into a patient's trachea, air is conducted from the source of compressed air through the channel 13, the valves 19, 20, 21, and the channel 14 and hole 22 to the cuff 12, which is thereby inflated and establishes sealing engagement with the wall of the trachea. The pressure applied for this purpose is so low that it cannot damage the mucous membrane of the trachea. When, during blowing of respiration air, the pressure in the end 11 of the trachea exceeds the pressure in the cuff, the sheet 21 closes the hole 19 so that the air in the cuff cannot escape. The respiration pressure now acts on the cuff side facing the lungs and increases the engagement pressure of the cuff. This increased engagement pressure, which may be damaging if applied for a prolonged period, is applied only during the short periods when the respiration pressure reaches its maximum.

Accordingly, the respiration catheter of the invention ensures effective sealing against the tracheal wall under all circumstances, also in case of lungs of low compliance requiring a high respiration pressure, and also ensures full perfusion of the tracheal wall since the engagement pressure is below the value which may cause damage, except for shorter periods.

The part of this channel positioned between the cuff 12 and the free end (not shown) of the channel 14 may be used for sucking liquid from the space between the catheter tube and the patient's trachea by connecting the free end with a suitable suction means (not shown).

In the second embodiment of the invention shown in FIGS. 3 and 4, the rectangular sheet 21 of the first embodiment has been replaced by a sheet ring surrounding the catheter tube and welded to the tube along the edges. This establishes two paths between the holes 19 and 20, and if the short path is blocked, e.g. in that the catheter tube engages the tracheal wall, air may pass the long way round the circumference of the catheter tube.

The invention is not restricted to the special embodiments shown and described above. For example, it is possible to arrange the holes 19 and 20 in the inwardly facing side of the channels 13 and 14 so that they open to the interior of the catheter tube, and consequently place the sheet 21 on the inner side of the catheter tube.

The cut-off valve may also be constructed differently from what is described above and may e.g. be formed by a sleeve or bladder of thin sheet material which connects the two ends of the channels 13 and 14 with each other. Also the shape and position of the channels may differ from what is shown and described.

I claim:

1. A respiration catheter tube for insertion into a patient's trachea, said catheter tube including a sealing cuff; said cuff having inflation means comprising a source of pressurized gas and an inflation tube, said inflation tube further comprising a cut-off valve; said cut-off valve having a portion responsive to pressure of respiratory gas downstream of said cuff and a portion interconnecting said pressurized gas in said inflation tube with pressurized gas within said cuff; said cut-off valve positioned at a distal end of said catheter tube; said inflation tube including two parts, a first part connected to said source of pressurized gas, and a second part communicating with said cuff, the two parts being interconnected through said cut-off valve; said cut-off valve having a first position and a second position, said first position comprising an open position with pressurized gas communicating through said inflation tube to said cuff, said second position comprising a closed position with communication of pressurized gas between said source of pressurized gas and said cuff being interrupted, said cut-off valve assuming said second position responsive to a pressure in the respiratory gas downstream of said cuff exceeding gas pressure in said inflation tube.

2. A respiration catheter according to claim 1, wherein the second part of said inflation tube having a first opening comprising said portion of said cut-off valve through which the second part communicates with the sealing cuff.

3. A respiration catheter according to claim 2, wherein the second part communicating with the sealing cuff has an extension towards a proximal end of the respiration catheter tube adapted to be connected to a source of respiration gas, said extension having on an outside thereof and in a vicinity of the sealing cuff a second opening, through which the extension communicates with exterior of the respiration catheter tube, the second part being closed between the second opening and the first opening preferably by a plug positioned in the second part.

4. A respiration catheter according to claim 2, wherein the cut-off valve is formed by an opening in said first part of said inflation tube, an additional opening in said second part of said inflation tube, and a sheet member placed across said opening in said first part of said inflation tube and said additional opening, said sheet member comprising that portion of said cut-off valve which is responsive to the pressure of respiratory gas downstream of said cuff so as to allow in said open position communication between the two parts and in said closed position, to interrupt the communication between the two parts of said inflation tube.

5. A respiration catheter according to claim 4, wherein the sheet member is ring shaped and encircles the respiration catheter tube.

* * * * *